United States Patent [19]

Greene, deceased et al.

[11] Patent Number: 5,090,428

[45] Date of Patent: Feb. 25, 1992

[54] PROTEIN COATED HAIR PROTECTION APPARATUS AND METHOD

[75] Inventors: Edward W. Greene, deceased, late of Portland, Oreg.; Barbara G. Jackson, heir, Tacoma Park, Oreg.

[73] Assignee: International Packagers, Inc., Lake Oswego, Oreg.

[21] Appl. No.: 383,858

[22] Filed: Jul. 20, 1989

[51] Int. Cl.$^5$ .............................................. A45D 7/04
[52] U.S. Cl. ..................... 132/204; 132/203; 132/207; 132/222; 424/71
[58] Field of Search ............ 132/202, 203, 204, 205, 132/207, 221, 222; 424/70, 71

[56] References Cited

U.S. PATENT DOCUMENTS

| | | | |
|---|---|---|---|
| 2,018,367 | 10/1935 | Lackenbach | 132/220 |
| 2,274,170 | 2/1942 | Stanley | 132/221 |
| 2,314,932 | 3/1943 | Gossaux | 132/221 |
| 2,631,593 | 3/1953 | Madore | 132/222 |
| 2,832,357 | 4/1958 | Powers | 132/221 |
| 2,839,066 | 6/1958 | Sanders | 132/221 |
| 2,869,559 | 1/1959 | Moore | 132/203 |
| 2,991,790 | 7/1961 | Bonilla | 132/207 |
| 3,087,502 | 4/1963 | Rosmarin | 132/221 |
| 3,354,039 | 11/1967 | Lukesch et al. | 167/87.1 |
| 3,683,939 | 8/1972 | Johnsen et al. | 132/202 |
| 3,837,349 | 9/1974 | Jedzinak et al. | 132/207 |
| 3,957,065 | 5/1976 | Busch et al. | 132/204 |
| 4,206,196 | 6/1980 | Davis | 132/202 |
| 4,600,028 | 7/1986 | Edman et al. | 132/222 |
| 4,632,132 | 12/1986 | Bustance et al. | 132/333 |
| 4,660,580 | 4/1987 | Hoch et al. | 132/204 |
| 4,848,377 | 7/1989 | Bires et al. | 132/207 |

FOREIGN PATENT DOCUMENTS 98854 8/1979 Japan ................... 132/221

*Primary Examiner*—John J. Wilson
*Assistant Examiner*—Frank A. LaViola
*Attorney, Agent, or Firm*—Klarquist, Sparkman, Campbell, Leigh and Whinston

[57] ABSTRACT

A method and apparatus for the protection of hair from permanent wave chemicals is disclosed. To accomplish protection, paper sheets are coated with protein. The protein is applied in an amount efficient to enable protein delivery from the sheets to the hair during the permanent wave process. Preferably, a composition containing about 45-65% by weight protein is applied to the sheets so that each sheet is about 20-60% by weight protein. The protein chemically protects the hair from structural damage during the permanent wave process in a highly effective manner.

17 Claims, 2 Drawing Sheets

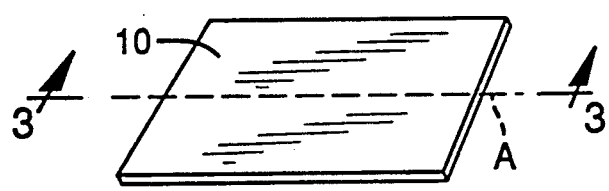
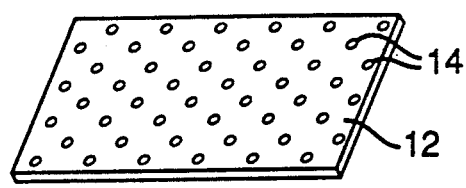
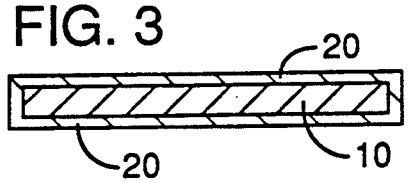
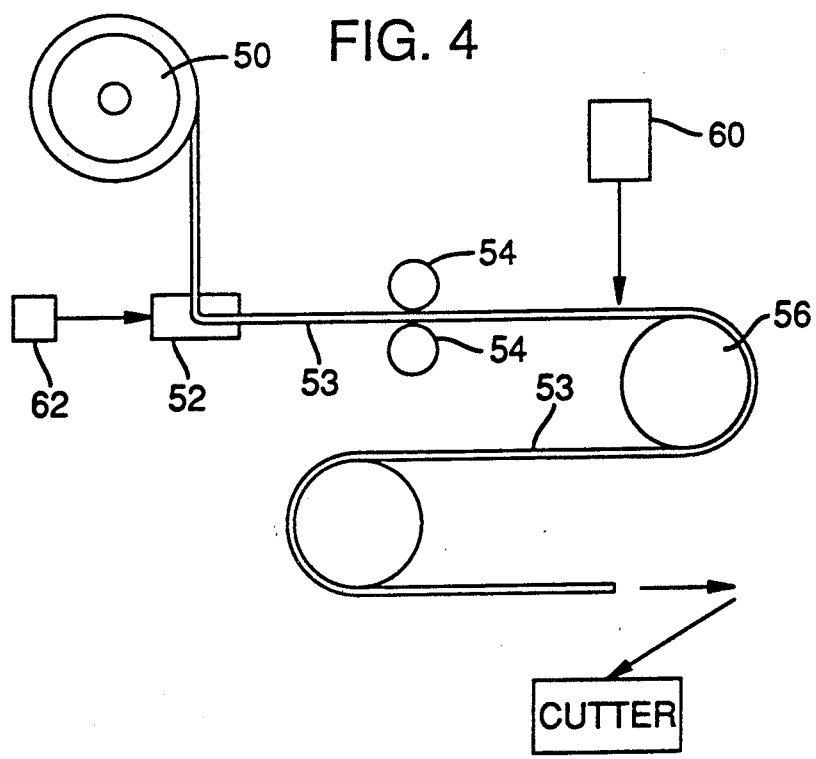

PROTEIN COATED HAIR PROTECTION APPARATUS AND METHOD

BACKGROUND OF THE INVENTION

The present invention generally relates to materials and methods used in permanent wave processes, and more particularly to a composition and method designed to chemically protect the hair during the application of permanent wave solutions and neutralizers.

For many years, permanent wave treatments have been used by men and women to obtain new and different hair styles. These treatments typically involve the application of a permanent wave solution which chemically disrupts the disulfide bonds of the hair so that it may be styled in a desired configuration. Following application of the permanent wave solution, a neutralizer is applied which terminates the chemical action of the wave solution.

A wide variety of permanent wave solutions exist which are typically combined with buffers, conditioners, wetting agents, and other ingredients known in the art. Commonly used wave solutions include chemicals such as ammonium thioglycolate and ammonium monothioglycolate. Conventional neutralizers include hydrogen peroxide, acetic acid, and sodium bromate. In addition, many other chemicals known in the art may be used as wave solutions and neutralizers. U.S. Pat. Nos. 2,018,367 and 3,837,349 both describe additional materials used in permanent wave processes.

However, permanent wave chemicals frequently cause damage to the hair during use. Hair consists of a protein matrix having a hollow, shaft-like configuration. During the permanent wave process, the protein structure of the hair may be damaged due to the strong chemicals involved. As a result, the external appearance of the hair can be adversely affected. It is therefore desirable to protect the hair during the permanent wave process so that damage is prevented.

In the past, a variety of protective compositions have been developed to minimize hair damage during the permanent wave process. For example, U.S. Pat. No. 3,957,065 discloses a liquid solution comprising a waving agent combined with keratein and a hair-softening agent (e.g. sodium carbonate, borax, ammonia, ammonium carbonate, and thioglycerin.)

U.S. Pat. No. 2,832,357 discloses permanent wave end papers which are saturated with lanolin.

U.S. Pat. No. 2,839,066 discloses permanent wave end papers impregnated with an oleaginous material (e.g. fatty quaternary ammonium compounds containing one or more lower alkyl groups.)

U.S. Pat. No. 3,354,039 involves a film-forming agent used in the permanent wave process which consists of urea cross-linked polypeptides derived from gelatin.

Notwithstanding the materials and methods indicated above, a need remains for a system designed to efficiently protect the protein structure of hair during the application of permanent wave chemicals. The present invention satisfies this need, as described herein below.

SUMMARY OF THE INVENTION

It is an object of the present invention to provide a method and apparatus for the protection of hair from permanent wave chemicals.

It is another object of the invention to provide a method and apparatus for the protection of hair during permanent wave processes which is easy to use and highly effective.

It is another object of the invention to provide a method and apparatus for the protection of hair during permanent wave processes which uses readily available materials.

It is a still further object of the invention to provide a method and apparatus for the protection of hair during permanent wave processes which prevents damage to the hair protein structure during chemical application.

It is an even further object of the invention to provide a method and apparatus for the protection of hair during permanent wave processes which uses specially treated paper in a unique process.

In accordance with the foregoing objects, a method and apparatus for the protection of hair from permanent wave chemicals is disclosed. To accomplish protection, flexible moisture permeable paper sheets are coated with a protein-containing composition and the protein coating is free of permanent wave chemicals. The protein composition is applied in an amount sufficient to enable the sheets to release protein upon the application of permanent wave solution. In a preferred embodiment, a solution containing about 45-65% by weight hydrolyzed protein is applied to the sheets so that each sheet after processing contains about 20-60% by weight protein. As a result, a substantial amount of protein is available for delivery during the permanent wave process. The released protein chemically protects the hair from structural damage in a highly effective manner.

These and other objects, features, and advantages of the invention shall become apparent from the following Detailed Description of a Preferred Embodiment and Drawings provided herein.

BRIEF DESCRIPTION OF THE DRAWINGS

FIG. 1 is a perspective view of a protein-treated paper sheet manufactured in accordance with the invention.

FIG. 2 is an alternative embodiment of the paper sheet illustrated in FIG. 1.

FIG. 3 is a longitudinal cross-sectional view of the paper sheet of FIG. 1.

FIG. 4 is a schematic illustration of the processing steps used to manufacture the paper sheets described herein.

DETAILED DESCRIPTION OF A PREFERRED EMBODIMENT

Figure 5:
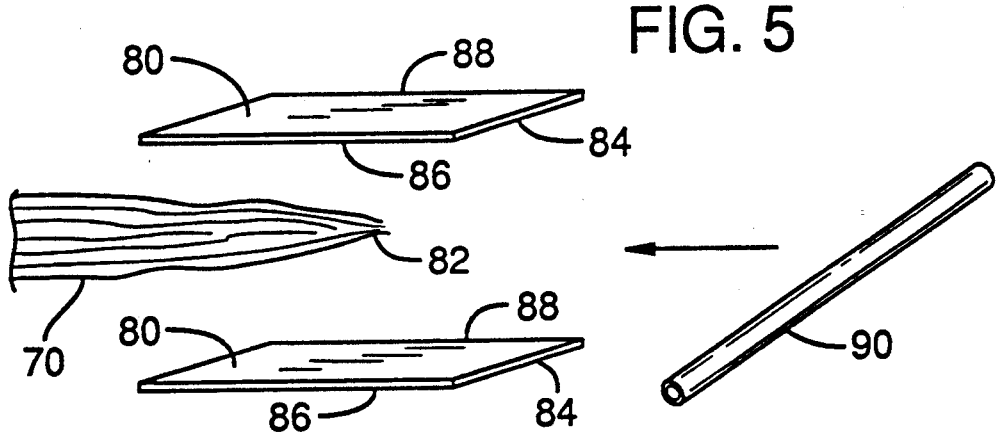
FIGS. 5-7 illustrate the application of paper sheets to the hair of a user during the permanent wave process.

The present invention involves a hair protection system designed for use in permanent wave processes. It is especially effective in protecting the protein structure of hair during the application of permanent wave chemicals and neutralizers.

In accordance with the invention, specially treated paper sheets are provided which are applied to the hair during the permanent wave process. Specific details regarding the application and use of the treated sheets will be described below in the section entitled "Application and Use".

Treated Paper Sheets: Composition and Construction

With reference to FIG. 1, a treated paper sheet 10 produced in accordance with the invention is illustrated. The sheet 10 is preferably manufactured of a thin, tissue-like paper which is strong, yet absorbent so that the sheet is moisture permeable. A variety of different paper products may be used having these characteristics. However, it is preferred that the paper have a high tensile and wet strength. In accordance with these goals, the paper should be comprised substantially of virgin (non-recycled) long fiber wood pulp, with the individual fibers being arranged in parallel rows. In addition, the rows and individual fibers within the paper will preferably have a parallel orientation relative to the longitudinal axis "A" of the sheet 10 as illustrated in FIG. 1. This orientation greatly increases the strength of the sheet 10, and minimizes tearing during the permanent wave process.

While the present invention shall not be limited to any single variety of paper, a preferred paper product is manufactured by the Ecusta Co. (division of P. H. Glatfelter Co.) of Pisgah Forest, N.C. This material has the characteristics shown below in Table I:

TABLE I

| Characteristic | Level |
| --- | --- |
| Basis Weight (g/M$^2$) | 15.9–18.1 |
| Tensile Strength (Kg/3 cm) | 3.8–5.5 |
| Aged Wet Tensile Strength (Kg/cm$^3$) | 2.0–3.3 |
| Thickness (cm) | approx. 0.00155 (in.) |

(Data obtained at 72 degrees F. and 50% relative humidity.)

These physical characteristics produce a sheet 10 with desirable strength qualities which are especially suited for use with permanent wave chemicals.

With reference to FIG. 2, an alternative embodiment of the sheet 10 shown in FIG. 1 is illustrated. In FIG. 2, a sheet 12 is provided which includes a plurality of evenly distributed holes 14 therethrough to increase the moisture permeability of such sheet. In a preferred embodiment, each of the holes 14 is approximately 0.02 inches in diameter, with 49 holes per square inch. However, the number and size of the holes 14 may be varied as desired. Sheets 10 and 12 work equally well in the present invention, with the selection of a particular sheet involving purchaser preference.

The sheets 10, 12 are cut to a size which is easily used in the permanent wave process. Each sheet 10, 12 typically ranges from 2×3 in. to 4×6 in., (2.5×4 in.=preferred).

The sheets 10, 12 are chemically treated to provide hair protection from permanent wave chemicals. Specifically, each sheet is coated with a liquid protein composition on one or both sides (preferred) with the resultant coating being free of any permanent wave chamicals. The steps used to accomplish coating will be described below in the section entitled "Manufacturing." In a preferred embodiment, a hydrolyzed animal protein solution containing about 45–65% by weight protein is used to coat sheets 10, 12. Hydrolyzed animal protein is traditionally produced by the enzyme hydrolysis of collagen-rich raw materials. Hydrolysis may also be accomplished by chemical, thermal, or high-pressure processes known in the art. However, enzyme hydrolysis is preferred in that it produces a product with a low ash content and a light color. While the use of a hydrolyzed protein solution represents a preferred embodiment of the invention, and the invention shall not be limited to the use of hydrolyzed protein only.

An exemplary protein solution suitable for coating the paper sheets described above is manufactured by the Geo. A. Hormel Co. of Austin Minn. and sold under the name "Peptein 2000." This material is a liquid solution which contains about 55% by weight hydrolyzed animal protein, with the balance consisting of water. It is produced from high-collagen raw materials, and will readily penetrate through the cuticle layer of human hair into the cortex, eventually becoming part of the hair shaft. Further characteristics of the Peptein 2000 product are listed below in Table 2:

TABLE 2

| CHARACTERISTIC | VALUE |
| --- | --- |
| Color (Gardner as is) | 12 (max.) |
| Viscosity | 100 cps (max.) |
| Specific Gravity | 1.15 (min.) |
| pH (2 to 1 dilution) | 5.8–6.3 |
| Molecular weight | 1500–2000 |
| Total Solids | 55% (min.) |
| Total Nitrogen | 8–10% |
| Ash | 2% (max.) |
| Iron | 5 ppm (max.) |
| Copper | 3 ppm (max.) |
| Aerobic Plate Count | less than 1000/gm |
| Gram Negative Rods | Negative |
| Gram Positive Rods | Negative for *Staph aureus* |

As indicated above, the protein composition is applied to one or both sides of the paper sheets 10, 12 in order to produce the final product in the form of a coated sheet having a coating thereon whose major constituent is protein material. FIG. 3 shows a longitudinal cross sectional view of the sheet 10 of FIG. 1 which is equally coated on both sides with a layer 20 of protein which after drying consists substantially entirely of protein material and contains no permanent wave chemicals. In a preferred embodiment, the total thickness of the coated sheet 10 in FIG. 3 will be about 0.002 in. If a sheet 10 is used having an initial thickness of about 0.00155 in. as noted above, each side of the sheet 10 is FIG. 3 will have a layer 20 of protein approximately 0.000225 in. thick. Further details involving production of the protein-coated sheets in accordance with the invention will be presented below in the "Manufacturing" section.

Tests have shown that the coated paper sheets will preferably consist of about 20–60% by weight protein when completed. Sheets containing less than about 20% by weight protein may not properly deliver sufficient amounts of protein to the hair during the permanent wave process. In addition, sheets containing more than about 60% by weight protein will be excessively tacky, making the sheets difficult to dispense and use. Also, sheets containing about 20–60% by weight protein have a high protein release factor during use. The term "protein release factor" involves the amount of protein which is capable of leaving the paper during use. For example, it has been experimentally shown that a coated paper sheet containing 45% by weight protein will have a protein release factor of 88%. Specifically, about 88% of the protein on the sheet will be released during the permanent wave process. The remaining 12% is bound to and within the fibrous matrix of the paper.

Manufacturing

FIG. 4 schematically illustrates the process steps used to produce protein-coated sheets in accordance with the invention. First, uncut paper substrate material 50 (which is normally provided in a large roll about 22 in. in diameter) is passed through a bath 52 of protein preferably having the composition characteristics described above. The bath 52 is maintained at room temperature (about 68–72 degrees F.) The protein-coated paper 53 is then drawn through pinch rollers 54 in order to remove excess protein from the paper 53. Next, the paper 53 is passed over a heated drum 56 maintained at a temperature of about 170-180 degrees F. in order to dry the paper 53.

Immediately prior to heating, an optional release agent 60 may be added to the coated paper 53. The release agent functions as an anti-sticking composition so that the final product does not stick together. The use of a release agent 60 becomes increasingly important when the paper 53 contains protein levels in the upper regions of the 20-60% range described above. Suitable release agents usable in the invention include water-soluble silicone materials known in the art, including a product sold by the Dow Corning Company under the name "Dow Corning 36 Emulsion". Other commercially available release agents include a product manufactured by the General Electric Company under the name "SM 2162", and by the Union Carbide Company under the name "LE 45". In a preferred embodiment, the release agent 60 is a combined with water in a 1:30 to 1:60 volume ratio (release agent:water). Normally, the release agent 60 is applied to only one side of the paper 53.

In addition, an optional surfactant 62 may be added to the bath 52 of protein. The surfactant 62 prevents the liquid in the bath 52 from foaming excessively as the paper is drawn therethrough. The surfactant 62 may be selected from a variety commercially available antifoaming agents known in the art. For example, a suitable surfactant 62 usable in the invention is manufactured by Vining Industries, Inc. of Lake Oswego, Oreg. under the name "Vinbrake 1367". Another suitable surfactant is a product sold by the Hercules Chemical Company of Wilmington, Del. under the name "Brick 7".

In a preferred embodiment, the paper is processed at a rate of 20-25 ft./min. After the paper 53 is dried using the heated drum 56, it is cut into small portions of a selected size (e.g. 2.5×4 in.). The portions are then appropriately packaged for sale.

Application and Use

Figure 6:
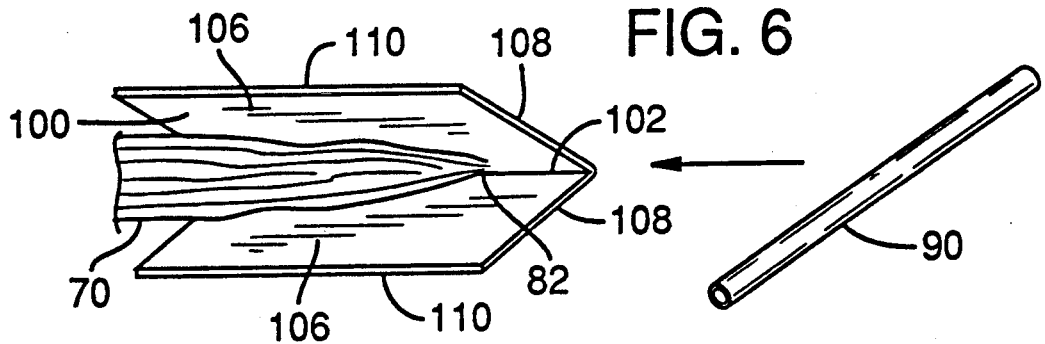
Figure 7:
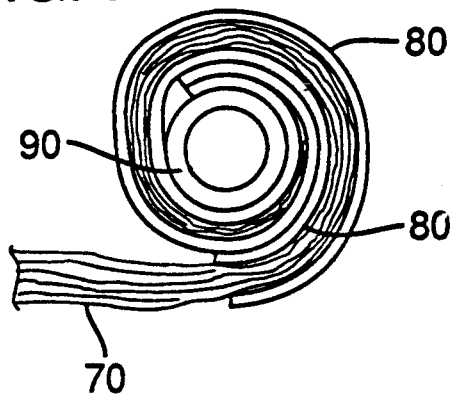

Use of the treated papers described herein is illustrated in FIGS. 5-7. With reference to FIG. 5, a lock 70 of hair is positioned between two sheets 80 of the coated paper 10 with the end 82 of the lock 70 being oriented so that it does not extend beyond the outer edges 84, 86, 88 of each sheet 80. The sheets 80 are then urged together with the lock 70 therebetween and rolled around a permanent wave rod 90 known in the art. The rolled lock 70 of hair is illustrated in FIG. 7, with the size of the rod 90 determining the diameter of the resulting curl. A larger rod 90 will produce a larger curl, and vice versa.

Alternatively, as shown in FIG. 6, the lock 70 of hair may be positioned between a single sheet 100 of the coated paper 10 which has been folded along its longitudinal axis 102 to divide the sheet 100 into two portions 106 of equal size as illustrated. Again, the end 82 of the lock 70 should not extend beyond the outer edges 108 and 110 of the sheet 100. The hair is then rolled as indicated above.

Next, one of many commercially-available permanent wave solutions is applied to the rolled hair. These solutions may contain a variety of active ingredients, including ammonium thioglycolate, ammonium monothioglycolate, dithiothreitol, dithioerythritol, mercaptans, and the like. Commercially available permanent wave kits having a wave solution and neutralizer with which the invention may be used include products manufactured by Faberge Inc. of New York, N.Y. under the trademark "Permette", The Wella Corporation of Englewood, N.J. under the trademark "Natural and Nice", and NaturElle, Inc. of Chicago, Ill. under the trademark "Natural Apple." However, the invention described herein shall not be limited to any specific commercial product, and is widely applicable to many other commercial materials.

Application of the wave solution wets the protein-containing sheets, causing release of the protein onto the hair. The released protein protects the individual hair shafts from damage caused by the wave solution in a manner which has yet to be scientifically determined. However, it is theorized that the released protein interacts with the hair structure at both the surface and molecular levels to protect the hair from chemical degradation. Specifically, cationic (+) charges of the applied protein are bound to the negative charges of keratin proteins in hair. Since permanent wave chemicals are known to dramatically increase the negative charge characteristics of hair, the affinity of hair for positively-charged protein is greater during the permanent wave process. As a result, substantial amounts of protein are attracted to the hair following the application of permanent wave chemicals which prevent the hair from becoming dry and brittle.

The wave solution is allowed to remain on the hair for about 7-30 minutes, depending on the type of chemicals used and the desired hair style. Also, heat may be applied during this period, depending on the chemicals involved. Finally, the hair is unrolled and the paper sheets discarded. The hair is then rinsed with a neutralizer known in the art which stops the chemical action of the wave solution. Typical neutralizers include hydrogen peroxide, sodium bromate, and acetic acid. The wave process is substantially completed at this point, with the protein-treated papers effectively protecting the hair from damage in a unique and efficient manner.

Having herein described a preferred embodiment of the invention, it is anticipated that suitable modifications may be made thereto by individuals skilled in the art within the scope of the invention. Accordingly, the invention shall only be construed relative to the following claims:

I claim:

1. A hair treatment apparatus for protecting hair from permanent wave solution chemicals comprising:
   a flexible paper sheet made substantially entirely of paper to be water permeable and having first and second sides; and
   a protein coating on at least one of said sides of said sheet, said coating containing a protein material as its major constituent and being free of permanent wave solution chemicals and releasing protein therefrom upon contact with said permanent wave solution.

2. The apparatus of claim 1 wherein said paper sheet is coated on both sides with the protein coating.

3. The apparatus of claim 1 wherein said paper sheet has a tensile strength of about 3.8-5.5 Kg/cm$^3$.

4. A hair treatment apparatus for protecting hair from permanent wave solution chemicals comprising:
   a flexible paper sheet which is moisture permeable having first and second sides; and a protein coating on at least one of said sides of said sheet, said coating containing a protein material as its major component and being substantially free of permanent wave solution chemicals and releasing protein therefrom upon contact with said permanent wave solution, said sheet with said protein coating thereon comprising about 20–60% by weight protein.

5. The apparatus of claim 4 wherein said protein coating comprises hydrolyzed animal protein.

6. An apparatus for protecting hair from permanent wave solution chemicals comprising:

a flexible paper sheet having first and second sides, said paper sheet being moisture permeable and comprised of virgin long wood pulp fibers oriented in a parallel relationship to a longitudinal size of said sheet, said sheet having a tensile strength of about 3.8–5.5. Kg/cm$^3$; and a protein coating on at least one of said sides of said sheet, said coating consisting substantially entirely of protein material and releasing protein therefrom upon contact with said permanent wave solution, said sheet with said protein coating thereon comprising about 20–60% by weight protein.

7. A permanent hair wave application method comprising the steps of:

separating said hair into at least one lock of hair;

positioning said lock adjacent at least one flexible paper sheet which is water permeable, said sheet having first and second sides and a protein coating on at least one of said sides, said coating containing a protein material as a major constituent and being free of permanent wave chemicals;

rolling said sheet and said lock together onto a rod member;

applying a permanent wave-producing chemical solution to said sheet and said lock, said applying of said permanent wave-producing chemical solution causing protein to be released from said sheet onto said hair for protection thereof;

unrolling said sheet and said lock from said rod member; and applying a neutralizer to said lock, said neutralizer, terminating wave-producing action of said permanent waveproducing chemical.

8. The method of claim 7 wherein said positioning of said lock adjacent at least one flexible paper sheet comprises placing said lock between two flexible paper sheets, one sheet being oriented above said lock, and the other sheet being oriented below said lock.

9. The method of claim 7 wherein said positioning of said lock adjacent at least one flexible paper sheet comprises folding said sheet along its longitudinal axis into two portions of equal size and placing said lock between said portions.

10. The method of claim 7 wherein said sheet is coated on both sides with the protein coating.

11. The method of claim 7 wherein said sheet has a tensile strength of about 3.8–5.5 Kg/cm$^3$.

12. A permanent hair wave application method comprising the steps of:

separating said hair into at least one lock of hair;

positioning said lock adjacent at least one flexible paper sheet which is water permeable, said sheet having first and second sides and a protein coating on at least one of said sides which contains a protein material as its major constituent and is free of permanent wave chemicals, said sheet comprising about 20–60% by weight protein;

rolling said sheet and said lock together onto a rod member;

applying a permanent wave-producing chemical solution to said sheet and said lock, said applying of said permanent wave-producing chemical solution causing protein to be released from said sheet onto said hair for protection thereof;

unrolling said sheet and said lock from said rod member; and applying a neutralizer to said lock, said neutralizer terminating wave-producing action of said permanent wave-producing chemical.

13. The method of claim 12 wherein said positioning of said lock adjacent at least one flexible paper sheet comprises placing said lock between two flexible paper sheets, one sheet being oriented above said lock, and the other sheet being oriented below said lock.

14. The method of claim 12 wherein said positioning of said lock adjacent at least one flexible paper sheet comprises folding said sheet along its longitudinal axis into two portions of equal size and placing said lock between said portions.

15. A permanent hair wave application method comprising the steps of:

separating said hair into at least one lock of hair;

positioning said lock adjacent at least one flexible paper sheet having first and second sides, said paper sheet being moisture permeable and comprised of virgin long wood pulp fibers oriented in a parallel relationship to a longitudinal axis of said sheet, said sheet having a tensile strength of about 3.8–5.5 Kg/cm$^3$, said sheet further comprising a protein coating on at least one of said sides consisting substantially entirely of protein material, said sheet comprising about 20–60% by weight protein;

rolling said sheet and said lock together onto a rod member;

applying a permanent wave-producing chemical solution to said sheet and said lock, said applying of said permanent wave-producing chemical solution causing protein to be released from said sheet onto said hair for protection thereof;

unrolling said sheet and said lock from said rod member; and applying a neutralizer to said lock, said neutralizer terminating wave-producing action of said permanent waveproducing chemical.

16. The method of claim 15 wherein said positioning of said lock adjacent at least one flexible paper sheet comprises placing said lock between two flexible paper sheets, one sheet being oriented above said lock, and the other sheet being oriented below said lock.

17. The method of claim 15 wherein said positioning of said lock adjacent at least one flexible paper sheet comprises folding said sheet along its longitudinal axis into two portions of equal size and placing said lock between said portions.

* * * * *